US012605475B2

(12) United States Patent
Tegel et al.

(10) Patent No.: US 12,605,475 B2
(45) Date of Patent: Apr. 21, 2026

(54) SANITIZING APPARATUS FOR CARD EXCHANGE

(71) Applicants: Robert G. Tegel, Orangeville, IL (US); Turan Erdogan, Kingston, MA (US); David H. Adams, Chesterfield, MO (US)

(72) Inventors: Robert G. Tegel, Orangeville, IL (US); Turan Erdogan, Kingston, MA (US); David H. Adams, Chesterfield, MO (US)

( * ) Notice: Subject to any disclaimer, the term of this patent is extended or adjusted under 35 U.S.C. 154(b) by 672 days.

(21) Appl. No.: 18/113,695

(22) Filed: Feb. 24, 2023

(65) Prior Publication Data

US 2023/0285611 A1  Sep. 14, 2023

Related U.S. Application Data

(60) Provisional application No. 63/319,410, filed on Mar. 14, 2022.

(51) Int. Cl.
| | |
|---|---|
| *A61L 2/00* | (2006.01) |
| *A61L 2/10* | (2006.01) |
| *A61L 2/26* | (2006.01) |
| *A61N 5/00* | (2006.01) |
| *B65G 11/04* | (2006.01) |

(Continued)

(52) U.S. Cl.
CPC *A61L 2/10* (2013.01); *A61L 2/26* (2013.01); *A61L 2202/11* (2013.01); *A61L 2202/122* (2013.01); *A61L 2202/123* (2013.01); *A61L 2202/14* (2013.01)

(58) Field of Classification Search
CPC .......... A61L 2/24; A61L 2/10; A61L 2202/11; A61L 2202/14; A61L 2202/122; A61L 2202/20; G01N 23/00
USPC ............... 422/24; 209/261, 900; 250/453.11, 250/454.11, 455.11, 492.1; 193/8, 35 R, 193/35 MD; 198/348
See application file for complete search history.

(56) References Cited

U.S. PATENT DOCUMENTS

| | | | |
|---|---|---|---|
| 7,397,041 B1* | 7/2008 | Leonard | A61L 2/10 250/455.11 |
| 10,850,184 B1* | 12/2020 | Colvin | A61L 2/24 |
| 11,040,271 B1* | 6/2021 | Sines | A61L 2/10 |

(Continued)

FOREIGN PATENT DOCUMENTS

| | | |
|---|---|---|
| AU | 2020100584 | 5/2020 |
| AU | 2020101409 | 8/2020 |

(Continued)

*Primary Examiner* — Monzer R Chorbaji
(74) *Attorney, Agent, or Firm* — Louis S. Horvath

(57) ABSTRACT

An apparatus for exposing a flat card to sanitizing radiant energy, has an enclosure that has an exposure chamber having a source of sanitizing radiation. A first insert slot and a second insert slot, disposed along an input surface of the enclosure are each configured to accept insertion of the flat card. A transport apparatus defines a first transport path to convey the flat card from the first insert slot, and through the exposure chamber, to emerge from a first output that opens on a first side surface of the enclosure and a second transport path to convey the flat card from the second insert slot, and through the exposure chamber, to emerge from a second output that opens on a second side surface of the enclosure that is opposite the first side surface.

20 Claims, 9 Drawing Sheets

(51) Int. Cl.
　　*B65G 37/00*　　　　(2006.01)
　　*G01N 21/00*　　　　(2006.01)

(56)　　　　　　　References Cited

U.S. PATENT DOCUMENTS

| | | | |
|---|---|---|---|
| 11,833,266 B2 * | 12/2023 | Whittemore | .............. A61L 2/24 |
| 2009/0252646 A1 * | 10/2009 | Holden | .................... A61L 2/10 |
| | | | 422/186.3 |
| 2009/0314956 A1 | 12/2009 | Long | |
| 2011/0233276 A1 | 9/2011 | Buchert | |
| 2018/0117192 A1 | 5/2018 | Baranov et al. | |
| 2019/0291149 A1 * | 9/2019 | Damskov | .............. B08B 7/0057 |
| 2022/0233735 A1 * | 7/2022 | Whittemore | .............. A61L 2/10 |
| 2023/0148035 A1 * | 5/2023 | Ayala | ........................ A61L 2/10 |
| | | | 422/24 |

FOREIGN PATENT DOCUMENTS

| | | | | |
|---|---|---|---|---|
| AU | 2021101605 | | 5/2021 | |
| KR | 101185153 | B1 | 9/2012 | |
| KR | 20130000082 | U | 1/2013 | |
| WO | WO 2021194526 | * | 9/2021 | .............. A61L 2/10 |

\* cited by examiner

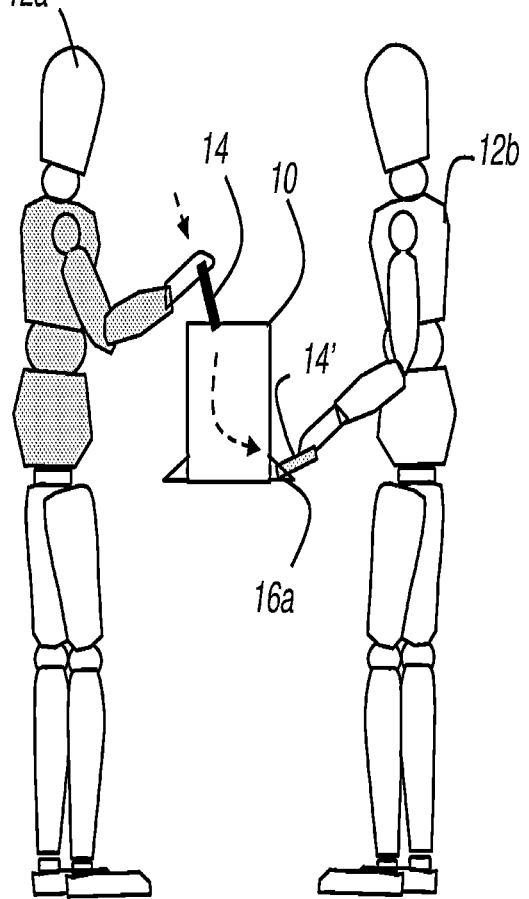
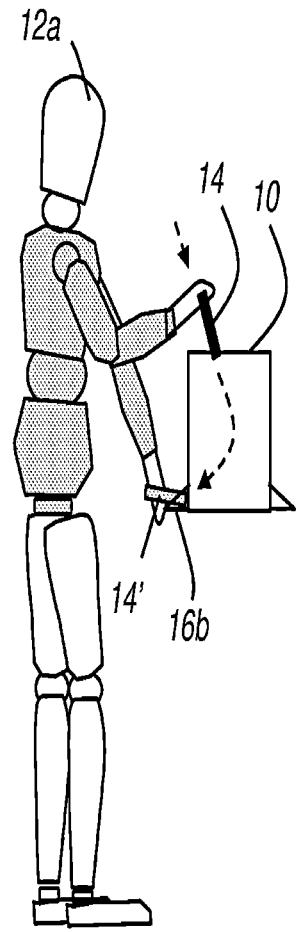
FIG. 1A          FIG. 1B

Operator interface

SANITIZING APPARATUS FOR CARD EXCHANGE

CROSS REFERENCE TO RELATED APPLICATIONS

This application claims the benefit of U.S. Provisional Application No. 63/319,410 provisionally filed on Mar. 14, 2022, entitled "SANITIZING APPARATUS FOR CARD EXCHANGE", in the names of Robert G. Tegel, Turan Erdogan, and David H. Adams, incorporated herein in its entirety.

FIELD

The present disclosure generally relates to apparatus and methods for sanitizing personal items and more particularly for methods and apparatus using ultraviolet (UV) radiation for sanitizing various types of cards or documents that are exchanged between parties in commercial transactions.

BACKGROUND

Personal objects, particularly those carried and handled by a subject, are acknowledged to be likely carriers for pathogens, often affording a ready path for disease transmittal from one person to another. In many types of commercial transaction, a flat card of some type is often passed between two parties, generally between a customer and an employee or clerk. Credit cards, hotel pass cards, personal identification (ID) cards, playing cards, membership cards, business cards, event or facilities access passes or tickets, currency, and other types of hand-held flat card items can be exchanged between two parties and handled by each of them, leading to a potential risk of communicating infection between them.

Various methods have been proposed and used to protect both parties in such transactions from infection caused by contact with passed cards, token cards, electronic keys or passes, and other hand-held documents. Approaches to addressing this potential risk have included use of chemical sprays, ultraviolet (UV) exposure chambers, and other devices for sanitizing or decontamination of card surfaces.

Conventional solutions, however, can require significant discipline on the part of one or both parties handing cards in a transaction and faithful adherence to rigid rules that can be inadvertently or intentionally bypassed, compromising the intended sanitizing or decontamination goal. Moreover, unintended exposure to harsh cleaning chemicals or to UV radiation leakage that can effectively sanitize card surfaces can have harmful effects on those involved in handling and cleaning cards in a commercial environment.

The commercial hotel desk is one exemplary environment for which a compact and user-friendly sanitizing apparatus would be particularly desirable. Credit cards, identification credentials, and electronic hotel room passes are routinely exchanged for handling between the customer and the hotel desk staff. Design goals for an apparatus for card sanitizing in this and similar environments would include:

(i) Ease of use, with intuitively obvious operation, minimizing the need for training and minimizing effects of operator error.

(ii) Speed of operation, able to sanitize the flat card without requiring more than a few seconds of wait time at most and able to sanitize multiple cards, including cards for different recipients, at the same time.

(iii) Simplicity of item transfer, with straightforward access for jam clearance or to resolve other difficulty.

(iv) 2-way function: Able to sanitize a card in transfer between two parties in both directions.

(v) Single-user return function: Able to sanitize cards, as well as currency, or other small documents for personal use.

In addition, proper containment of the exposure radiation is needed in order to prevent exposure of those using the apparatus.

It can be appreciated that there is a need for an apparatus that sanitizes or decontaminates credit cards, electronic access passes, identification materials, and other personal flat-card items supporting a commercial transaction for routine transfer between a customer and another person.

SUMMARY

The Applicants address the problems listed in the background section for providing controlled UV sanitizing exposure to credit cards, credentials such as a driver's license, electronic access passes, and other personal articles for sanitizing using high-energy UV light. Embodiments of the present disclosure can provide a UV exposure solution that can be particularly effective in supporting commercial transactions and facilities access, for example.

According to an embodiment of the present disclosure, there is provided an apparatus for exposing a flat card to sanitizing radiant energy, comprising:

an enclosure that comprises:

(a) an exposure chamber having a source of sanitizing radiation;

(b) a first insert slot and a second insert slot, each slot disposed along an input surface of the enclosure and each configured to accept insertion of the flat card;

(c) a transport apparatus that defines:

(i) a first transport path that is configured to convey the flat card from the first insert slot, and through the exposure chamber, to emerge from a first output that opens on a first side surface of the enclosure;

(ii) a second transport path that is configured to convey the flat card from the second insert slot, and through the exposure chamber, to emerge from a second output that opens on a second side surface of the enclosure that is opposite the first side surface.

DRAWINGS

The foregoing and other objects, features, and advantages of the invention will be apparent from the following more particular description of the embodiments of the invention, as illustrated in the accompanying drawings. Elements of the drawings are not necessarily to scale relative to each other.

FIG. 1A is a schematic diagram showing operation of the Applicant's apparatus in a transfer mode.

FIG. 1B is a schematic diagram showing operation of the Applicant's apparatus in a self-use mode.

DETAILED DESCRIPTION

Figure 2:
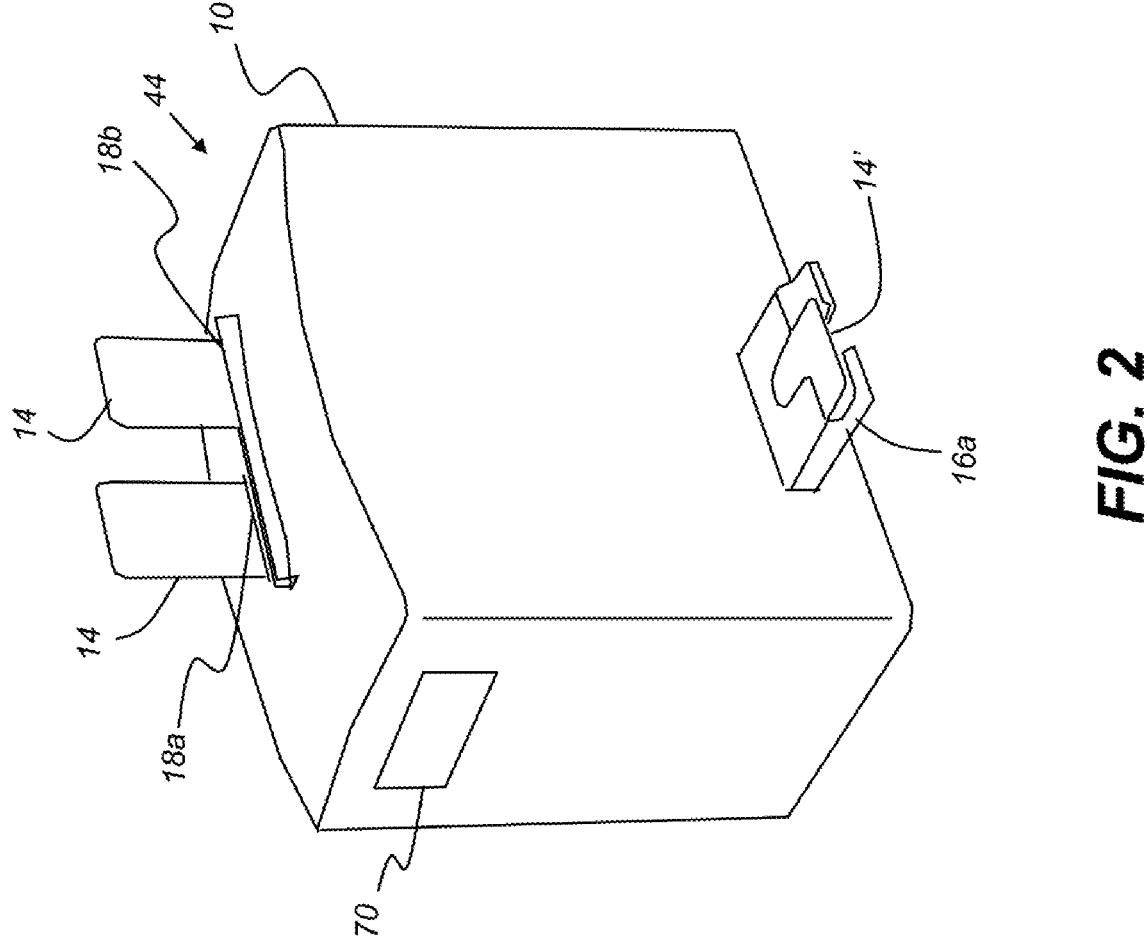
FIG. 2 is a perspective view that shows a sanitizing apparatus as a desktop unit in an exemplary embodiment.

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

The terms "user", "operator", "party" and "subject" may be used interchangeably in the present disclosure, and relate to any individual who introduces an article to, or removes an article from, the apparatus of the present disclosure for exposure processing.

As used herein, the term "energizable" relates to a device or set of components that perform an indicated function upon receiving power and, optionally, upon receiving an enabling signal. The word "exemplary" is used herein to mean "serving as an example, instance, or illustration." Any aspect described herein as "exemplary" is not necessarily to be construed as preferred or advantageous over other aspects.

The phrases "exposure radiation" or "sanitizing radiation" describe generated radiant energy that is at suitable levels for sanitizing material surfaces. For purposes of description, this energy is described herein as UV (ultraviolet) energy in a suitable spectral range for sanitizing, such as in the in the range of about 100 to 280 nm.

An embodiment of the present disclosure provides apparatus for controlled UV exposure of flat card items, such as credit cards, facilities access cards, identification cards and licenses, and other card-based or card-mounted personal articles, such as for sanitizing to render surfaces of the article substantially free of pathogens. It can be noted that the disclosed apparatus can have broader application to any of a number of functions that use exposure to UV or other high-energy radiant sources and can include various industrial applications, such as for rapid curing of various types of polymer materials on suitable surfaces, such as adhesives, for example. However, to provide comprehensive information, but without limitation, the description that follows illustrates the apparatus structure, components, and functions with relation to an embodiment for credit card or facilities-access keycard sanitization as examples that have particular utility.

The schematic diagrams of FIGS. 1A and 1B summarize alternative behaviors in using the Applicant's sanitizing solution. FIG. 1A shows a sanitizing apparatus 10 used in a transfer mode as a sanitizing mechanism to support a transaction between users 12*a* and 12*b*, such as between a hotel desk clerk and a customer. A card 14 is sanitized in sanitizing apparatus 10 as it passes from the first user 12*a* to the second user 12*b*. User 12*a* simply selects a particular input or insert slot that directs card 14 along a sanitizing exposure path for exposure and sanitizing to provide sanitized card 14'; the same path then transfers the card, as sanitized card 14', to output slot 16*a* for receipt by user 12*b*.

FIG. 1B shows an alternate but related use of sanitizing apparatus 10 in a self-use mode according to an embodiment of the present disclosure. Here, user 12*a* inserts a card 14 for cleaning and receives back sanitized card 14', which emerges from an output 16*b*, on an opposite surface of apparatus 10, but most convenient for user 12*a*.

Advantageously, sanitizing apparatus 10 allows both users 12*a* and 12*b* to sanitize items simultaneously, in either or both transfer (FIG. 1A) and self-use or self-return (FIG. 1B) modes.

The perspective view of FIG. 2 shows sanitizing apparatus 10 as a desktop unit in an exemplary embodiment. The user can choose either of two input or insert slots 18*a*, 18*b* on an input surface 44, depending on whether or not card 14 is for imminent use in a transaction with another person. When the user selects insert slot 18*a*, the sanitized card 14' is returned via output slot 16*a*. Alternately, where the user selects insert slot 18*b*, sanitized card 14' emerges from output slot 16*b* on the opposite side surface (not visible in the view of FIG. 2).

Figure 3A:
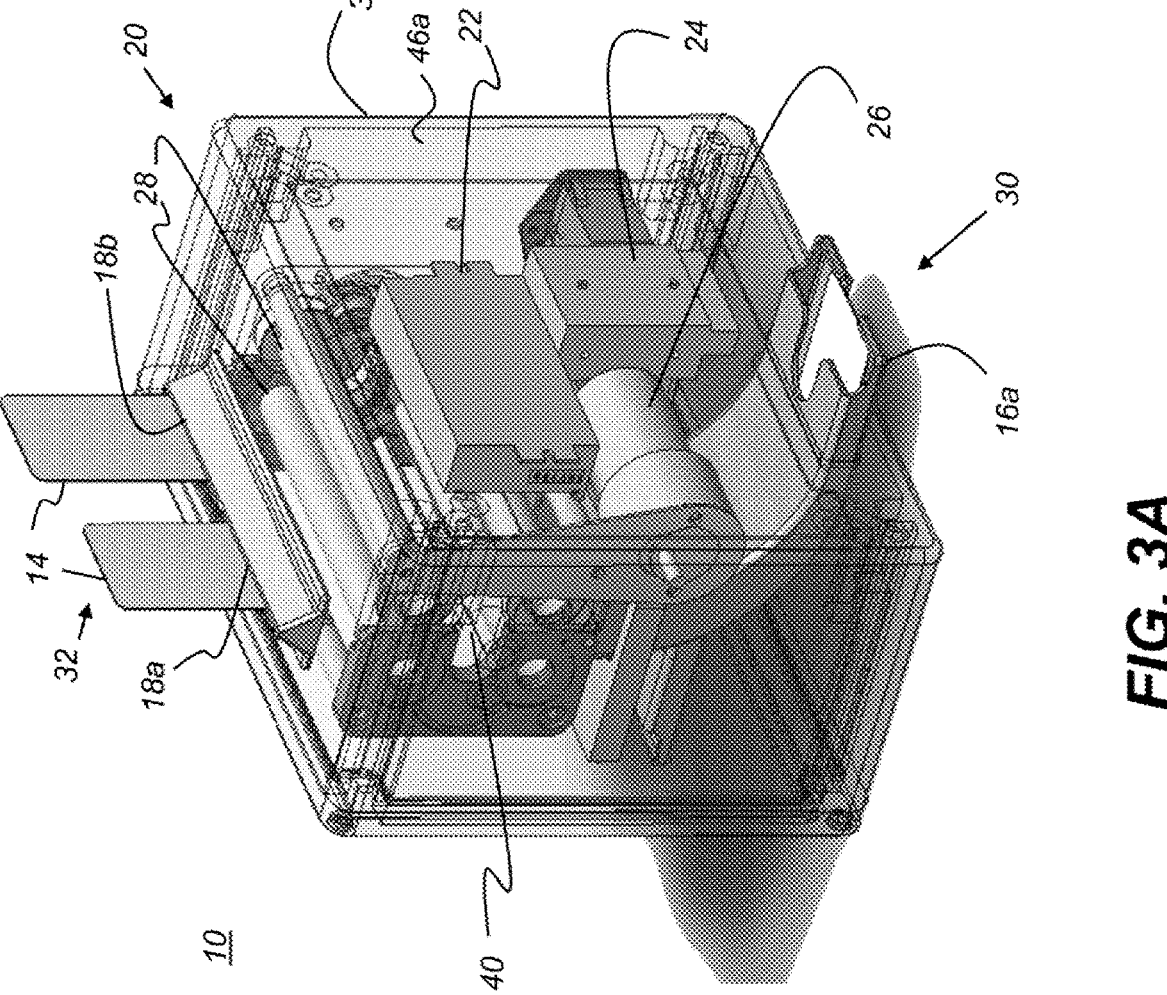
FIGS. 3A and 3B show perspective views of internal components of a sanitizing apparatus that lie within an enclosure according to an embodiment of the present disclosure.
Figure 3B:
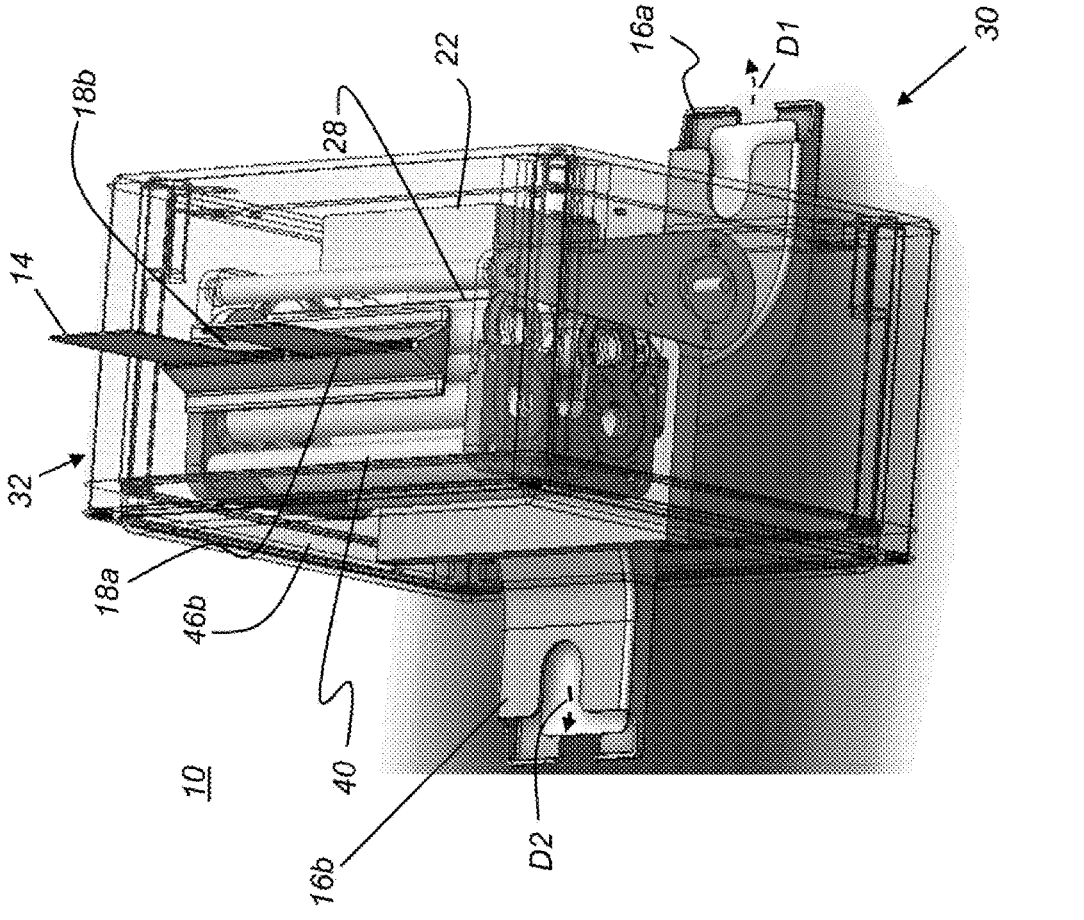

FIGS. 3A and 3B show perspective views of the internal components of sanitizing apparatus 10 that lie within an enclosure 34 (shown essentially transparent to allow visibility of internal components) according to an embodiment of the present disclosure. A ballast 22 provides power for the UV light source. Power supply 24 and motor 26 provide the motive drive power for a transport apparatus 20 that drives a series of rollers 28 for conveying card 14 through a UV exposure chamber 40, past the UV source, along a first transport path 30 emerging in a first direction at output slot 16*a* along a first side surface 46*a* or along a second transport path 32 emerging in an opposite direction at output slot 16*b* on the reverse side surface 46*b* (shown in FIG. 3B).

Alternately, additional electrical sensors and devices can be provided along the transport paths 30 and 32 for further control of apparatus 10 operation and timing. Thus, for example, a solenoid or cam/ratchet component can be positioned as a delay apparatus to temporarily delay feeding of a card object through a slot while another is being sanitized, or to control dwell time within exposure chamber 40. This would help to allow for adequate UV exposure for each card that is input. Control for coordination of mechanical movement and electrical component energization can be provided by an electrical sequencer or electronic controller mounted within enclosure 34, but not visible in FIGS. 3A-3C.

Figure 3C:
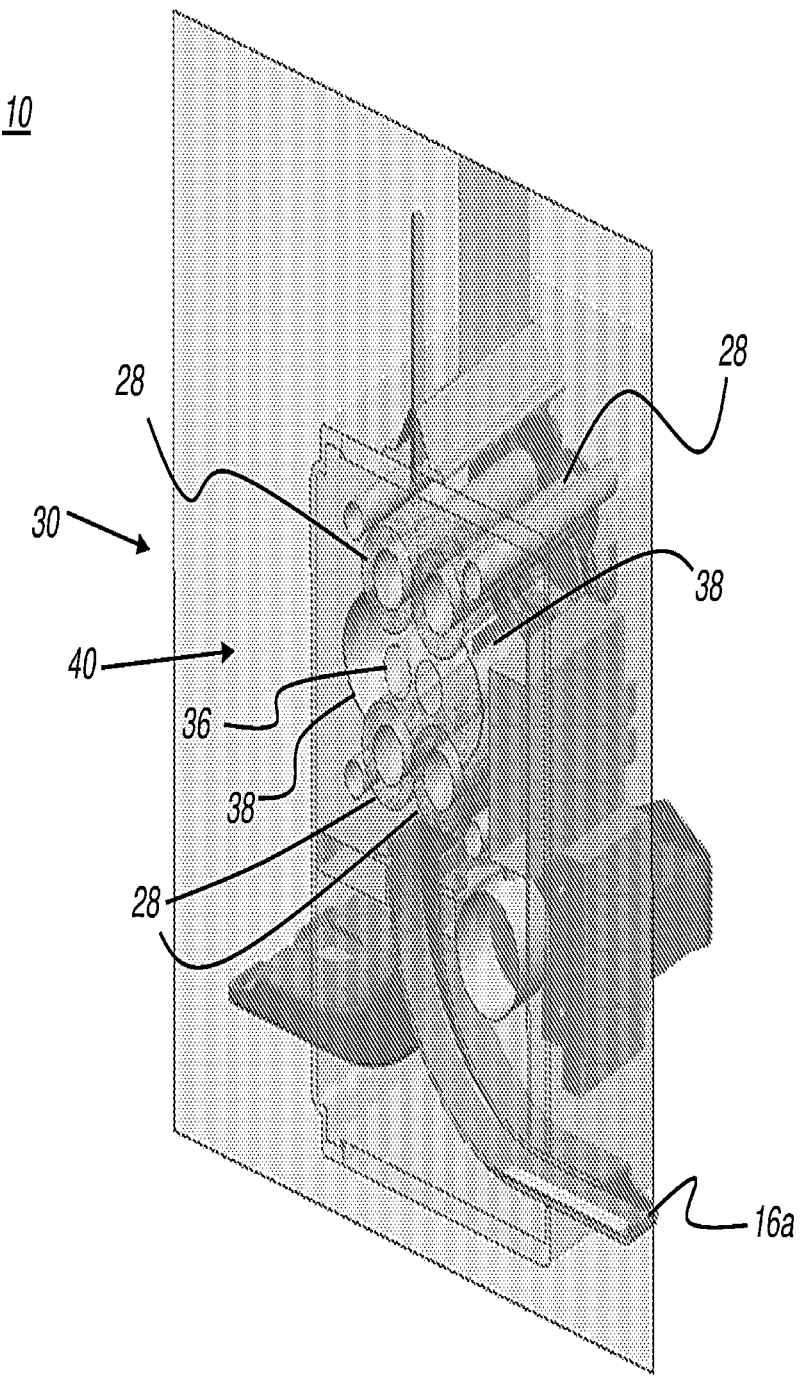
FIG. 3C is a cross-sectional view in perspective, showing relative positions of components within the transport path and exposure chamber.

FIG. 3C is a cross-sectional view in perspective, showing relative positions of components within transport path 30 and exposure chamber 40. A UV bulb 36 is disposed near the center of exposure chamber 40. Exposure chamber 40 is bounded by first and second curved reflectors 38. For receiving sanitizing exposure energy within a single exposure chamber 40, both transport paths 30 and 32 can share the same UV bulb 36 and receive light from the same set of reflectors 38. Both sides of the card 14 can be exposed simultaneously.

Figure 4:
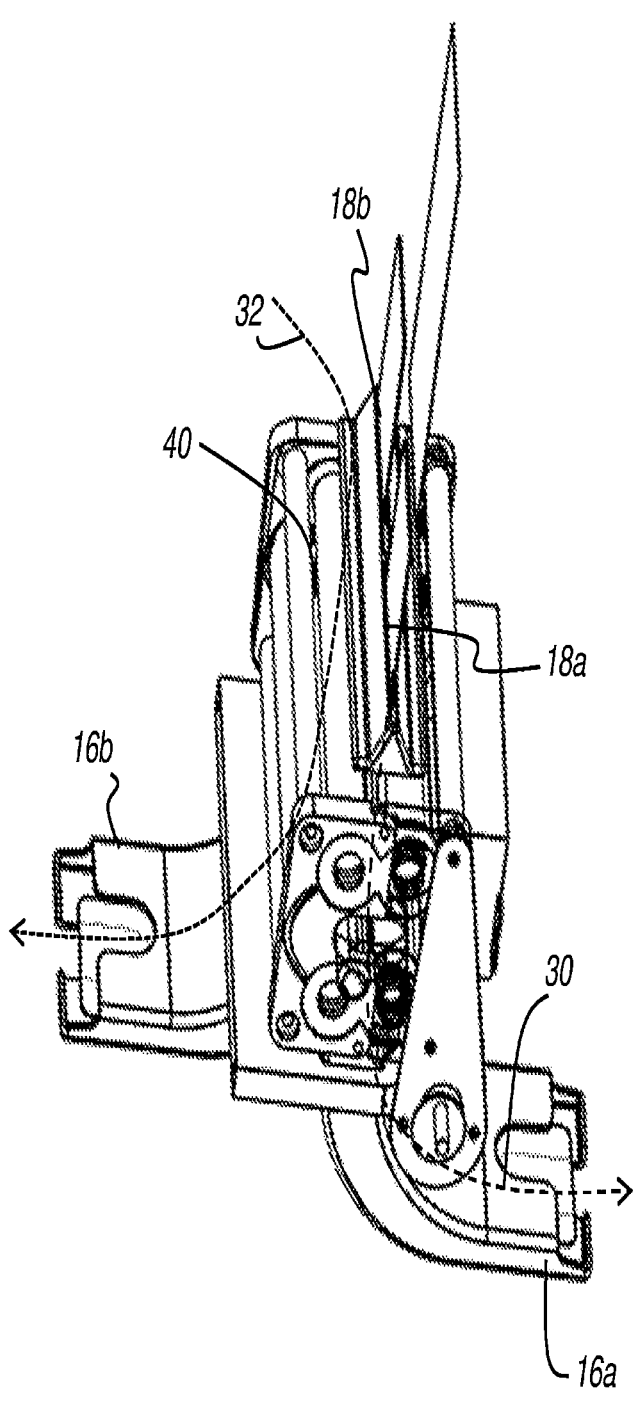
FIG. 4 is a perspective view showing exemplary transport path components.
Figure 5:
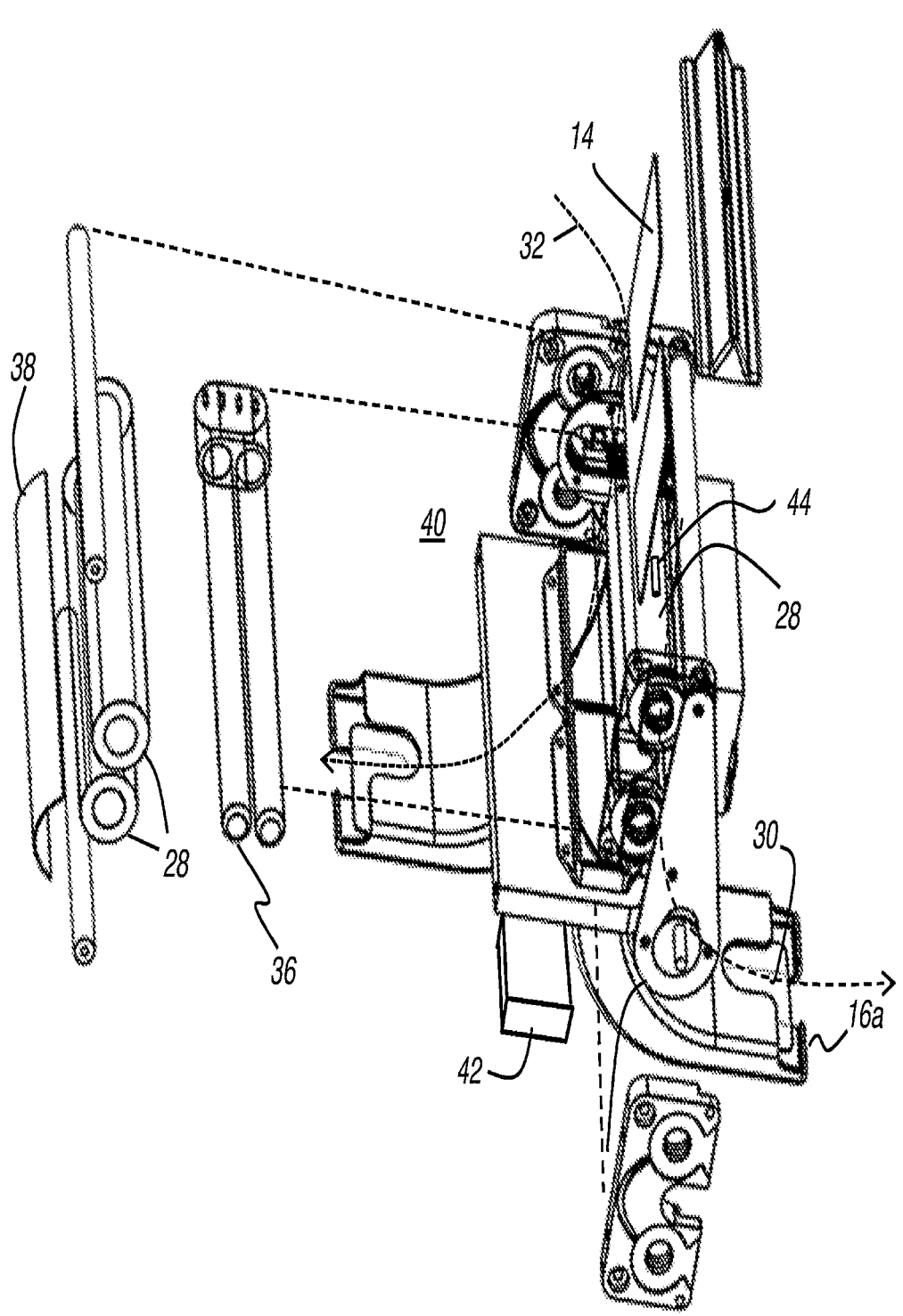
FIG. 5 is a partial exploded view showing component features of transport paths and the exposure chamber in more detail.

FIG. 4 shows components along transport paths 30 and 32. Transport paths 30 and 32 share a number of the components that convey card 14 along either path. Optional sensors can alternately be provided (for example, sensor 44 at an input slot, as shown in FIG. 5) for detecting card 14 insertion in either input slot 18*a* or 18*b* or for sensing and reporting progress along points of either path 30 or path 32. Sensors can be configured to provide a signal that actuates motor 26 directly or that indicates insertion activity to a control processor that is in communication with sanitizing apparatus 10 components for initiating motor control and exposure functions. A detection sensor signal can be used, for example, to actuate apparatus 10 upon card insertion to deliver sanitizing exposure as needed, including providing a "wake-up" signal that energizes one or both the sanitizing radiation source and the transport drive motor(s), for example.

As FIGS. 3A and 3C particularly show, motor 26 or other actuator can provide rotary motion for both first and second transport paths, with optional driving gears, belts, or other devices for transferring this motion to one or more of rollers 28. According to an embodiment of the present disclosure, rollers 28 transfer rotary motion to each other, without need for additional belts, gears, or other drive components. Rollers 28 can be configured to provide an appropriate amount of friction against the card 14 surface for controlling transport speed, and consequently exposure time as the card 14 descends into and passes through exposure chamber 40. Rollers 28 can optionally rotate at different speeds, in order to subject the surface(s) of the card to buffing by roller friction for enhanced sanitizing, as the card being sanitized travels along the transport path.

According to an embodiment of the present disclosure, rollers 28 can have a silicone surface that is configured for maintaining friction against the card 14 surface and also provides a measure of cleaning for the card 14 surface, such as being able to remove foreign material and fluids from card 14. As they rotate, rollers 28 themselves are sanitized by exposure to the UV light from bulb 36, minimizing or eliminating the need for cleaning or sanitizing the roller surfaces.

FIG. 5 is a partial exploded view showing component features of transport paths 30 and 32 and exposure chamber 40 in more detail. As the source of sanitizing radiation, bulb 36 can be a single, curved emissive bulb, a single tube having two lobes or bulb sections in an elongated U-shape with a gap between lobes, such as a TUV PL-L compact UVC germicidal lamp from Signify, Koninklijke Philips N.V. Alternately, chamber 40 may have one or more individual tubes that each extend in the direction of the rollers 28 and across each of the transport paths 30 and 32. For thorough, simultaneous exposure of both sides, card 14 can be conveyed through the gap between the lobes of bulb 36 or between individual tubes of bulbs 36.

A pair of reflectors 38, facing each other as best shown in FIG. 3C, can bound the sides of exposure chamber 40, helping to concentrate the emitted UV exposure energy within chamber 40, both for cards traveling through apparatus 10 and for roller 28 surfaces. The reflective surfaces may provide specular (mirror-like) reflection, diffuse reflection (such that light at a particular incident angle reflects or scatters into a substantial range of angles), or some combination of both specular and diffuse reflection. Examples of surface materials providing suitable specular reflection can include various polished metals, metallic thin-film coatings, or dielectric thin-film coatings. An exemplary surface material providing diffuse reflection can include polytetrafluoroethylene (PTFE).

Bulb 36 can be selectively de-energized, such as switched off when no card 14 is being sanitized, then energized as needed, such as when insertion of card 14 at either insert slot 18*a* or 18*b* is sensed.

Enclosure 34 is intended to shield users from exposure to the UV radiation. Enclosure 34 can be plastic, metal, or a composite material, for example. According to an embodiment of the present disclosure, enclosure 34 is formed of clear cell-cast acrylic or other polymer that is transparent to, or transmits, visible light, but is treated to filter out and absorb or otherwise block almost all of the harmful UVC exposure energy.

Transport speed through exposure chamber 40, or dwell time within exposure chamber 40, can be varied over a range, using a user interface control knob (not shown), for example. Typical transport speeds can be in the range between about 0.20 inches/second to about 2 inches/second, but could be outside this range, without limitation. Other speed values can be used; in some embodiments, the user can adjust a speed setting best suited to the type of card being exposed, considering factors such as relative card thickness or stiffness, card surface condition or finish, and the like.

As a useful auxiliary function, sanitizing apparatus 10 can provide additional air cleansing under UV light, during sanitizing operation or when idle, or at any time when UV bulb 36 is energized and emitting radiation. Apparatus 10 can include an optional ventilation fan 42 (FIG. 5) and can have ventilation features formed on sides of the enclosure or along its base, for example. Using these features, apparatus 10 can provide a ventilation path through enclosure 34 for sustained or controlled intake, exposure, and release of ambient air, while also helping to cool UV bulb 36 and other electrical components. Ventilation openings and one or more optional fans 42 can provide a continuous or periodic flow of air through exposure chamber 40, thus allowing the UV radiation to destroy airborne pathogens as well as those found on surfaces of flat cards and other personal articles. According to an alternate embodiment of the present disclosure, the air cleaning function operates primarily when apparatus 10 is idle or for a few minutes following card 14 exposure; however, simultaneously cleaning the surrounding air and sanitizing flat card articles can have clear advantages for more thorough decontamination at a site.

Operator Interface

Apparatus 10 can be configured for fully automatic operation, having one or more sensors that detect insertion of card 14 into one of the insert slots 18*a*, 18*b* and, upon detection, energize the UV bulb 36 and motor 26, for example. According to an embodiment of the present disclosure, as shown in FIG. 2, an operator interface 70 is provided for further control and monitoring of sanitizing apparatus 10, including status reporting to assist in reporting jam detection, need for bulb 36 replacement, roller slippage, or other condition that may require operator attention and correction.

Figure 6:
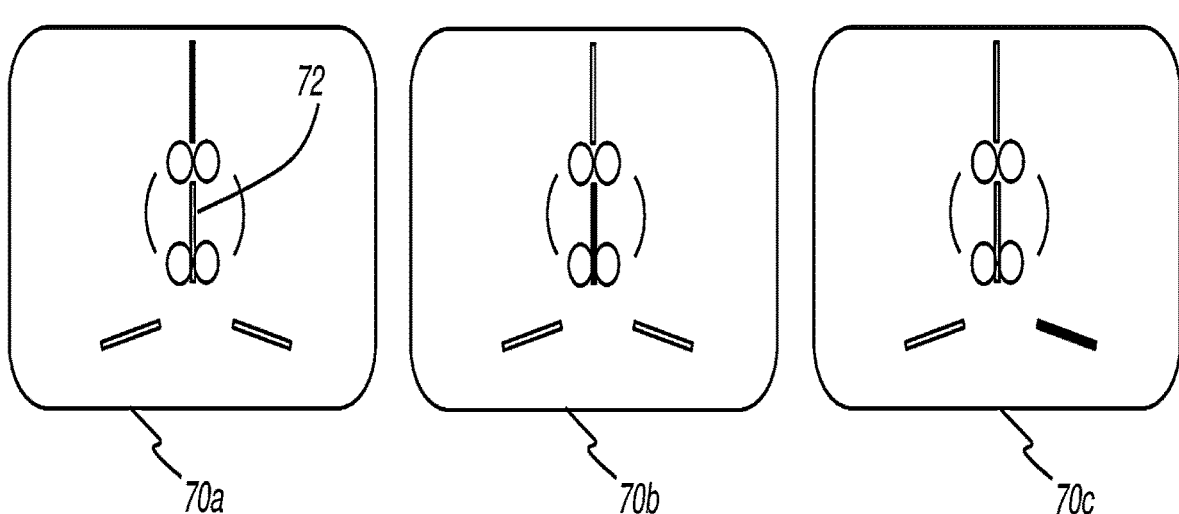
FIG. 6 shows an exemplary display interface for showing status of sanitizing apparatus operation.

FIG. 6 shows an exemplary display interface that can be energizable for showing status of sanitizing apparatus 10 operation. Example interfaces 70*a*, 70*b*, and 70*c* show displays for status reporting, schematically representing the overall position of card 14 along its transport path. Beginning with insertion at interface 70*a*, card 14 continues to exposure, as shown in iconic form at interface 70*b*, then to output at interface 70*c*. Flashing of card 14 icon 72 can indicate a jam condition or stuck roller, for example.

One or more windows (not shown) can be provided for showing card 14 progress through apparatus 10. Windows can be various materials fabricated or treated to filter out UV radiation.

Apparatus 10 can include an indicator that shows that UV bulb 36 is operative. An operator display can also provide time-elapsed values or time-remaining estimate.

OTHER EMBODIMENTS

Figure 7:
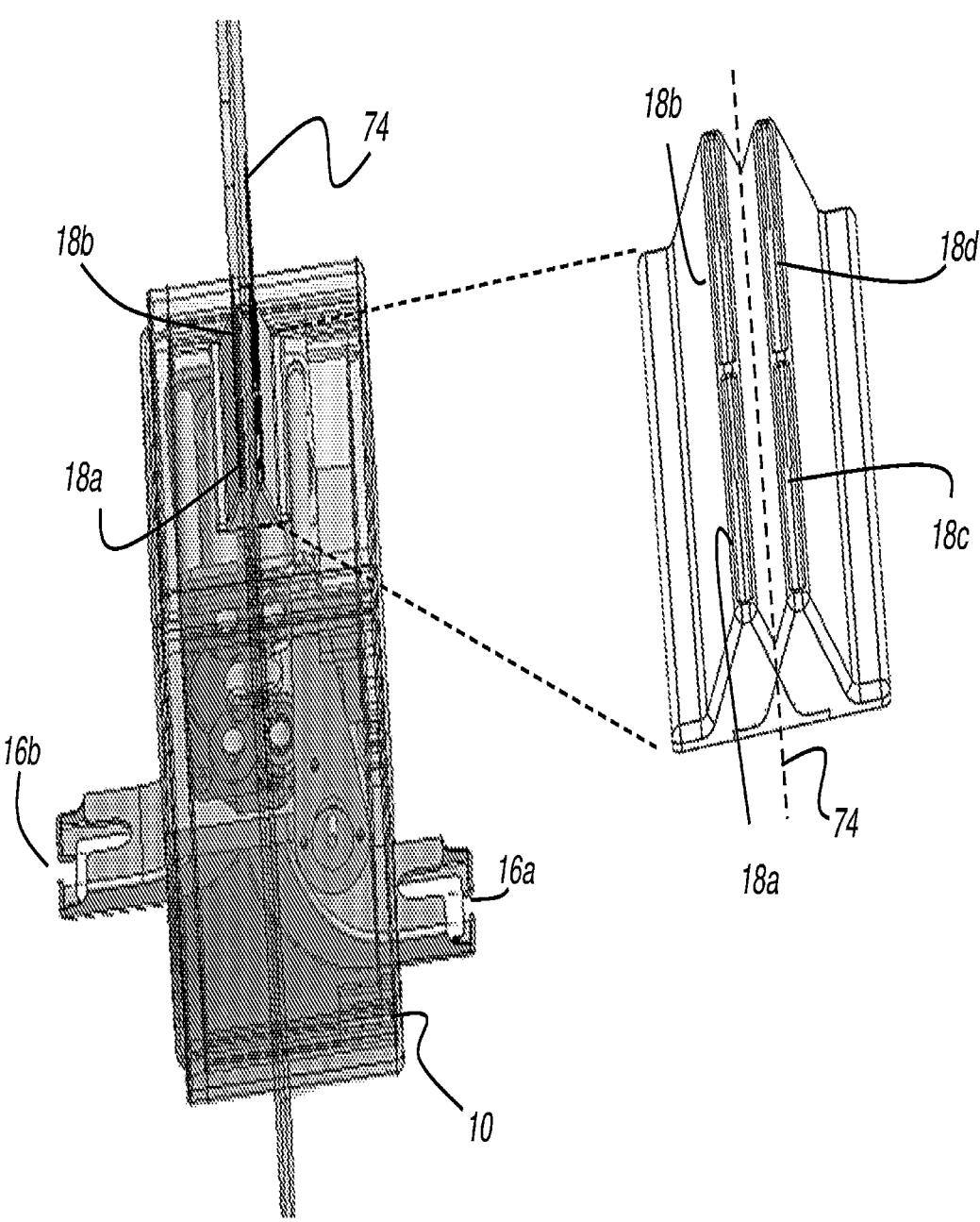
FIG. 7 is a perspective view that shows a sanitizer with a dividing window in an alternate embodiment.

The perspective view of FIG. 7 shows an alternate embodiment of sanitizing apparatus 10 in which users 12*a* and 12*b* (FIG. 1A) can be on different sides of a window or screen 74, such as behind a glass or acrylic screen, for example. As shown for better visibility in the enlarged portion of the FIG. 7 arrangement, one pair of insert slots 18*a* and 18*b* are on one side of screen 74; an additional pair of insert slots 18*c*, 18*d* can be provided on the other side of screen 74. The use of both transfer and return slots on each side of screen 74 allows both sanitized card transfer and self-use sanitizing for the user on each side of apparatus 10, without handling of the same input slots by both parties. Similar to the dual-input slot arrangement of FIGS. 2 through 5, each user has a single output slot for receiving sanitized cards.

Advantageously, apparatus 10 provides an exposure system that can minimize or eliminate the need for door handling for card insertion or removal by the users, for timing devices that indicate completion, or for providing door-related interlock devices to prevent both parties using the apparatus from inadvertent exposure, and requires no necessary contact with machine surfaces for exposure and transfer of a card or other suitable article. Insert slots 18*a*, 18*b* can be continuously visible and accessible, making use of the device straightforward. Apparatus 10 can run continuously, allowing a user the capability to load and unload cards 14 continuously, such as might be useful for sanitizing a stack of hotel room card keys at the end of a shift or periodically sanitizing other temporary access passes, for example. According to an embodiment of the present disclosure, a stacking device (not shown) can allow continuous feeding of successive cards 14 through the apparatus 10, such as for bulk sanitizing of cards, such as to sanitize gaming cards for casinos, for example.

Exposure effectiveness can also be enhanced by introducing one or more gases or other fluids into exposure chamber 40, such as at one or more intervals during the exposure cycle. The fluids introduced can be sanitizing, reactive, or inert.

One fairly effective approach sanitizes card 14 using Ultraviolet light (UV), particularly light in the UV-C range (nominally, with wavelengths in the range of about 100 to 280 nm). Radiant energy can be UV-C or other light energy that is effective for sanitizing.

Sanitizing apparatus 10 can optionally include scanner components, such as a chip reader, energizable for acquiring credit card or personal ID data from an inserted card.

The invention has been described in detail with particular reference to a presently preferred embodiment, but it will be understood that variations and modifications can be effected within the spirit and scope of the disclosure. The presently disclosed embodiments are therefore considered in all respects to be illustrative and not restrictive. The scope of the invention is indicated by any appended claims, and all changes that come within the meaning and range of equivalents thereof are intended to be embraced therein.

The invention claimed is:

1. An apparatus for sanitizing a flat card, the apparatus comprising:
   (a) an exposure chamber housed within an enclosure and having a source of sanitizing radiation;
   (b) a first insert slot and a second insert slot, each slot disposed along an input surface of the enclosure and each configured to accept insertion of the flat card; and
   (c) a transport apparatus that defines:
      (i) a first transport path that is configured to convey the flat card from the first insert slot and through the exposure chamber, to emerge from a first output that opens on a first side surface of the enclosure; and
      (ii) a second transport path that is configured to convey the flat card from the second insert slot and through the exposure chamber, to emerge from a second output that opens on a second side surface of the enclosure that is opposite the first side surface.

2. The apparatus of claim 1 wherein the enclosure is transparent to visible light.

3. The apparatus of claim 1 wherein the first and second transport paths pass through a gap in a single ultraviolet light source within the exposure chamber.

4. The apparatus of claim 1 wherein the transport apparatus simultaneously exposes both front and back surfaces of the flat card to the sanitizing radiation.

5. The apparatus of claim 1 wherein the transport apparatus further comprises one or more rollers and wherein at least a first roller is configured to remove foreign material from a surface of the flat card.

6. The apparatus of claim 1 wherein the enclosure further comprises a scanner that is configured to read encoded data from the flat card that is being conveyed along the first or second transport path.

7. The apparatus of claim 1 wherein the enclosure further comprises a third and a fourth insert slot for accepting the flat card item.

8. The apparatus of claim 1 further comprising an operator interface that is energizable to display status of the exposure.

9. The apparatus of claim 1 further comprising a sensor configured to generate a signal indicating insertion of the flat card into the first or second insert slot.

10. The apparatus of claim 9 wherein the transport apparatus is actuated upon receiving the sensor signal indicating insertion.

11. The apparatus of claim 1 wherein the exposure chamber further comprises surfaces that reflect the source radiation onto the first and second transport paths.

12. The apparatus of claim 1 wherein the transport apparatus comprises two or more rollers that rotate at different speeds.

13. The apparatus of claim 1 wherein the sanitizing radiation is ultraviolet light.

14. The apparatus of claim 1 wherein the enclosure further provides a ventilation path for intake, exposure, and release of ambient air.

15. A method for sanitizing a flat card, the method comprising:
   providing an enclosure having a first surface and a having second surface that is on an opposite side of the enclosure from the first surface and an input surface extending between the first surface and second surface, and further having a first insert slot on the input surface configured to accept a flat card intended for sanitizing and return to a first party and a second insert slot on the input surface configured to accept the flat card intended for sanitizing and transfer to a second party;

sensing insertion of the flat card in the first or second insert slot and providing an insertion signal;

in response to the insertion signal, energizing an internal transport apparatus to transport the flat card either:

(i) along a first transport path from the first insert slot to a first output along the first surface of the enclosure;

or (ii) along a second transport path from the second insert slot to a second output along the second surface of the enclosure;

and directing sanitizing radiation to the flat card in conveyance along either the first or second transport path.

16. The sanitizing method of claim 15 further comprising directing sanitizing radiation to cards being transported in both the first and second transport paths simultaneously.

17. The sanitizing method of claim 15 wherein the sanitizing radiation is ultraviolet light in the spectral range between 100 and 280 nm.

18. The sanitizing method of claim 15 further comprising providing a third insert slot and a fourth insert slot on the input surface and energizing the internal transport apparatus to transport the flat card inserted into the third insert slot through the sanitizing radiation to the second output along the second surface of the enclosure for return to the second party and the flat card inserted into the fourth insert slot through the sanitizing radiation to the first output along the first surface of the enclosure for transfer to the first party.

19. An apparatus for exposing a flat card to sanitizing radiant energy, comprising:

an enclosure that defines:

(i) a first transport path that is configured to convey the card from a first insert slot to a first output that opens on a first side of the enclosure, and (ii) a second transport path that is configured to convey the card from a second insert slot to a second output that opens on a second side of the enclosure that lies opposite the first side of the enclosure;

an internal exposure chamber within the enclosure and that is common to both the first and the second transport paths, wherein the exposure chamber is configured to direct UV exposure radiation onto opposite surfaces of the inserted flat card as the card is conveyed along either the first or second transport path by a transport drive, and a sensor that sends an actuation signal to the transport drive upon sensing insertion of the flat card at either the first or the second insert slot.

20. The apparatus of claim 19 further comprising a delay apparatus configured to temporarily delay card conveyance at the first or the second insert slot.

* * * * *